United States Patent
Tilton, Jr.

[11] Patent Number: 6,010,495
[45] Date of Patent: Jan. 4, 2000

[54] INSTRUMENTATION FOR ENDOSCOPIC SURGICAL INSERTION AND APPLICATION OF LIQUID, GEL AND LIKE MATERIAL

[76] Inventor: Eugene B. Tilton, Jr., 513 Dorrington Blvd., Metairie, La. 70005

[21] Appl. No.: 09/021,564

[22] Filed: Feb. 10, 1998

Related U.S. Application Data

[63] Continuation-in-part of application No. 08/718,861, Sep. 24, 1996, Pat. No. 5,797,899, which is a continuation-in-part of application No. 08/644,504, May 10, 1996, Pat. No. 5,766, 157, which is a continuation-in-part of application No. 08/625,098, Apr. 1, 1996, abandoned, which is a continuation-in-part of application No. 08/407,409, Mar. 17, 1995, Pat. No. 5,503,623.

[51] Int. Cl.⁷ ........................................ A61M 5/00
[52] U.S. Cl. ............................ 606/1; 604/28; 604/181
[58] Field of Search ........................... 600/563, 573; 606/1; 604/27, 28, 181, 186, 187, 264

[56] References Cited

U.S. PATENT DOCUMENTS

| | | | |
|---|---|---|---|
| 3,154,079 | 10/1964 | McKay | 604/264 |
| 4,722,725 | 2/1988 | Sawyer et al. | 604/44 |
| 4,729,764 | 3/1988 | Gaultier | 128/750 |
| 4,842,580 | 6/1989 | Oulette | 128/750 |
| 4,904,238 | 2/1990 | Williams | 604/264 |
| 4,936,834 | 6/1990 | Beck et al. | 604/264 |
| 4,966,162 | 10/1990 | Wang | 128/750 |
| 4,968,307 | 11/1990 | Dake et al. | 604/264 |
| 5,125,910 | 6/1992 | Freitas | 604/264 |
| 5,167,646 | 12/1992 | Swafford | 604/39 |
| 5,190,519 | 3/1993 | Mead et al. | 604/39 |
| 5,257,973 | 11/1993 | Villasuso | 604/49 |
| 5,263,927 | 11/1993 | Shlain | 604/13 |
| 5,295,952 | 3/1994 | Pietrafitta | 604/15 |
| 5,304,187 | 4/1994 | Green et al. | 604/13 X |
| 5,310,407 | 5/1994 | Casale | 604/59 |
| 5,419,777 | 5/1995 | Hofling | 604/264 |
| 5,533,986 | 7/1996 | Mottola et al. | 604/264 |

*Primary Examiner*—Max Hindenburg
*Attorney, Agent, or Firm*—Garvey, Smith, Nehrbass & Doody, L.L.C.

[57] ABSTRACT

A method and apparatus for endoscopic surgical insertion and application of a liquid, gel or like medicinal material enables a surgeon to utilize various delivery tubes with differing spray patterns to apply the desired material. In endoscopic surgery of the body cavity (including chest cavity and pelvis), instrumentation and surgical products are typically introduced through "ports" consisting of valves, sleeves or tubes. To properly and efficiently introduce and apply liquid, gel or like medicinal material, the present invention provides a method and apparatus for dispensing the desired material with a desired pattern or spray. The instrument consists of an elongated instrument body that can receive one of a selected flexible delivery tubes (of a kit of tubes) having a distal end with a nozzle. The instrument body rotates at its distal end, thereby rotating the dispensing tube. The selected nozzle of the selected dispensing tube can be positioned to dispense with a desired spray pattern into any rotational position of the patient's body cavity. A syringe (or a syringe with an extension tube can be used to push gel, liquid medicine or the like through the dispensing tube to the distal end thereof.

26 Claims, 7 Drawing Sheets

INSTRUMENTATION FOR ENDOSCOPIC SURGICAL INSERTION AND APPLICATION OF LIQUID, GEL AND LIKE MATERIAL

CROSS-REFERENCE TO RELATED APPLICATIONS

This is a continuation-in-part of copending U.S. Ser. No. 08/718,861, filed Sep. 24, 1996 now U.S. Pat. No. 5,797,897 which is a continuation-in-part of copending U.S. patent application Ser. No. 08/644,504, filed May 10, 1996 now U.S. Pat. No. 5,766,157 which is a continuation-in-part of copending U.S. patent application Ser. No. 08/625,098, filed Apr. 1, 1996 now abandoned, which is a continuation-in-part of U.S. patent application Ser. No. 08/407,409, filed Mar. 17, 1995 (now U.S. Pat. No. 5,503,623) which is incorporated herein by reference.

STATEMENT REGARDING FEDERALLY SPONSORED RESEARCH OR DEVELOPMENT

Not applicable

REFERENCE TO A "MICROFICHE APPENDIX"

Not applicable

BACKGROUND OF THE INVENTION

1. Field of the Invention

The present invention relates to a method and apparatus for endoscopic surgical (endo-surgical) introduction and application of liquid, gel, and like medicinal materials.

2. General Background of the Invention Surgery performed within a body cavity (e.g., chest cavity, abdominal cavity) by means of endoscopic surgery utilizes of one or more surgical entry "ports" in varying size. The majority of sizes is in the range of five (5) millimeters to fifteen (15) millimeters, but may be as small as approximately two (2) millimeters. Each port consists of a tube with proximal and distal ends. A valve structure on the proximal end of the port member allows instruments to be passed through the body cavity wall while maintaining appropriate intra-abdominal $CO_2$ pressure.

While instruments pass easily through the associated port member and its valve structure, liquids, gels, and like medicinal materials cannot be easily administered in endoscopic surgery.

In endoscopic surgery, there are or will be a variety of liquid, gel and like medicinal materials that require application in the body cavity (including the pelvis). Because these products have specific medical purposes (example: adhesion prevention and as a delivery vehicle) the application will have to be precise (to targeted areas or tissues) as opposed to the general way irrigating solutions are administered to wash or rinse tissues during surgery. Also, because these products will be expensive they cannot be wasted and precise application is desired.

Currently, liquids or solutions are usually administered through a common laparoscopy instrument called a suction/irrigator, aspiration/irrigator, irrigator, irrigating cannula, cannula or other similar terminology. These are simple straight tubes usually ranging from between about 3 mm and 5 mm in diameter with an opening on the distal end and possibly some holes on the side of the tube near that end.

Rinsing or irrigating fluids are flushed in to wash and moisten tissues. These simple tubes (usually metal or plastic) can also administer some liquid medical products though but not with precision or purpose and not in any specific, selected direction or specific, selected pattern. There are also long needles used for injection of medicines or retrieving of eggs from ovaries. However, these are simply an extension of the well-known standard injection needle. Such needles are for injection of liquid and medicines into tissues while the present invention is for applying liquid, gels and like medicinal materials onto the surface of tissues even if these products attach to or ultimately penetrate into the tissues.

A number of patents have issued for surgical instruments some of which contemplate endoscopic deployment. For example, U.S. Pat. No. 5,304,187 issued to David Green et al., and entitled "Surgical Element Deployment Apparatus", provides an apparatus which facilitates endoscopic deployment and positioning of surgical elements adjacent to body tissue for subsequent securement thereto. The surgical element is wound within a tubular sleeve and then extruded from the distal end of the tubular sleeve. A method is also disclosed for deploying and positioning surgical elements using the apparatus of the present invention.

The Pietrafitta U.S. Pat. No. 5,295,952, entitled "Swab For Laparoscopy" discloses a swab that comprises an outer generally tubular shank with a handle or gripping end and a working end. An inner shaft is slidably received in the shank and has a working end and a gripping end. A changeable, disposable absorbent tip is operably connected to the working end of the shaft. The swab includes a biasing means at the gripping ends of the shank and shaft for urging the absorbent tip toward the gripping ends.

In the Shlain U.S. Pat. No. 5,263,927, entitled "Apparatus And Methods For Dispensing Surgical Packing", a surgical packing dispenser is disclosed that comprises an elongate tube having a housing mounted on its proximal end. A continuous roll of sterilized packing material is disposed within the housing, and a free end of the packing material extends distally through the tube. The sterilized packing material is mounted on the spindle, and a handle is provided to rotate the spindle to feed material from the roll down the dispenser tube. In this way, relatively lengthy amounts of the packing material can be dispensed during laparoscopic and other endoscopic surgical procedures.

In the Villasuso U.S. Pat. No. 5,257,973, entitled "Sealing Sleeve And Method For Laparoscopy", a sealing sleeve is disclosed for use with a cannula in open laparoscopy. The sleeve of the subject invention has a conical shaped collar defining a passageway for feeding the cannula therethrough. The collar is formed of a resilient medically inert material capable of conforming to the edges of an incision thereby forming a gas tight seal and maintaining the pneumoperitoneum during the laparoscopy. The sleeve also includes a polygonal tube connected to the collar and rigid supports attached to the polygonal tube for receiving a suture to maintain the cannula in place with respect to the patient.

The Casale U.S. Pat. No. 5,310,407, entitled "Laparoscopic Hemostat Delivery System And Method For Using Said System", discloses a delivery system and method for inserting hemostatic material through a channel of a laparoscopic cannula, and for directly applying the material to an internal tissue site, includes a hollow sheath having a cross-section and configuration that permits sliding passage thereof through the channel of the laparoscopic cannula. The sheath is charged with hemostatic material, and the hemostatic material is advanced through the lumen of the sheath and mechanically applied at the tissue site by an applicator. The hemostatic material may be in the form of compressed loose fibers, a sponge, a powder, a paste, a sheet, or a combination thereof, and may be composed of resorbable collagen.

BRIEF SUMMARY OF THE INVENTION

The present invention provides an improved instrument for endoscopic surgical insertion and application of liquid, gel and like material and medicines. The present invention also provides a method of dispensing a liquid medicinal material into a patient's body cavity such as, for example, the abdominal cavity, chest cavity, or the like.

The present invention thus provides an improved surgical endoscopic or "endo-surgical" instrument. The apparatus includes a surgical tube that can be placed by a surgeon through a surgical opening in a patient's body cavity wall such as the abdominal wall or the chest cavity wall. The tube provides an elongated open ended bore.

An instrument body is provided that can be placed in the bore of the tube, the instrument body having proximal and distal end portions and a central longitudinal open ended bore.

A kit is provided that includes a plurality of dispensing tubes that each have proximal and distal end portions, each dispensing tube being sized and shaped to fit the instrument body bore and at least some of the dispensing tubes being flexible at least at the distal end portion thereof.

A nozzle is provided at the distal end portion of each of the dispensing tubes for dispensing liquids, gels, and like materials, including medicinal materials into a patient's body cavity.

The distal end of the instrument body includes a rotator that is rotatable into multiple positions, the rotator being coupled to the selected dispensing tube so that the distal end portion of the dispensing tube also rotates with the rotator.

A bore for transmitting between the proximal and distal end portions of each dispensing tube is provided even when the tube occupies the bore of the instrument body and the nozzle is positioned within the patient's body cavity.

BRIEF DESCRIPTION OF THE DRAWINGS

For a further understanding of the nature and objects of the present invention, reference should be had to the following detailed description, taken in conjunction with the accompanying drawings, in which like parts are given like reference numerals, and wherein.

DETAILED DESCRIPTION OF THE INVENTION

Figure 1:
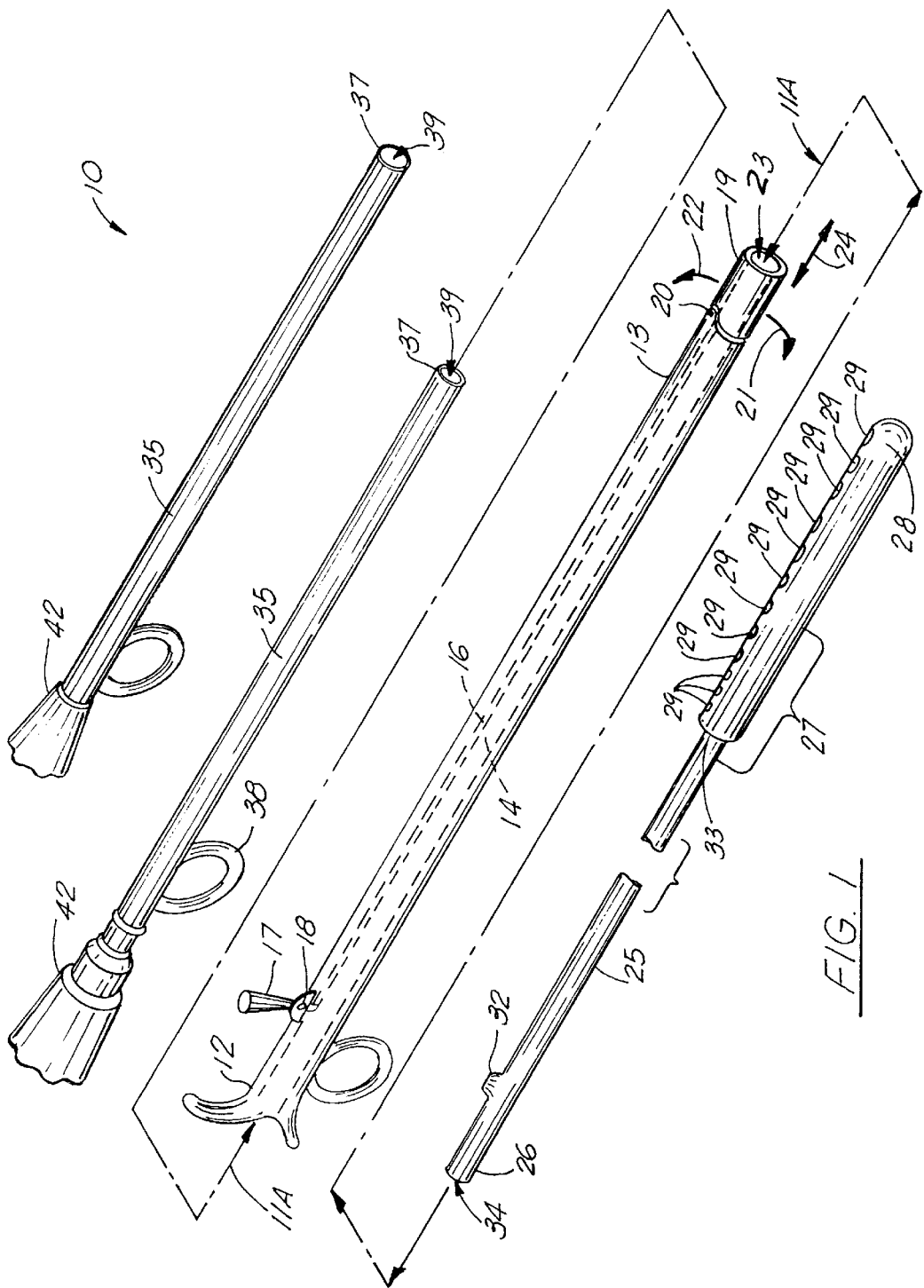
FIG. 1 is a perspective exploded view of the preferred embodiment of the apparatus of the present invention.
Figure 2:
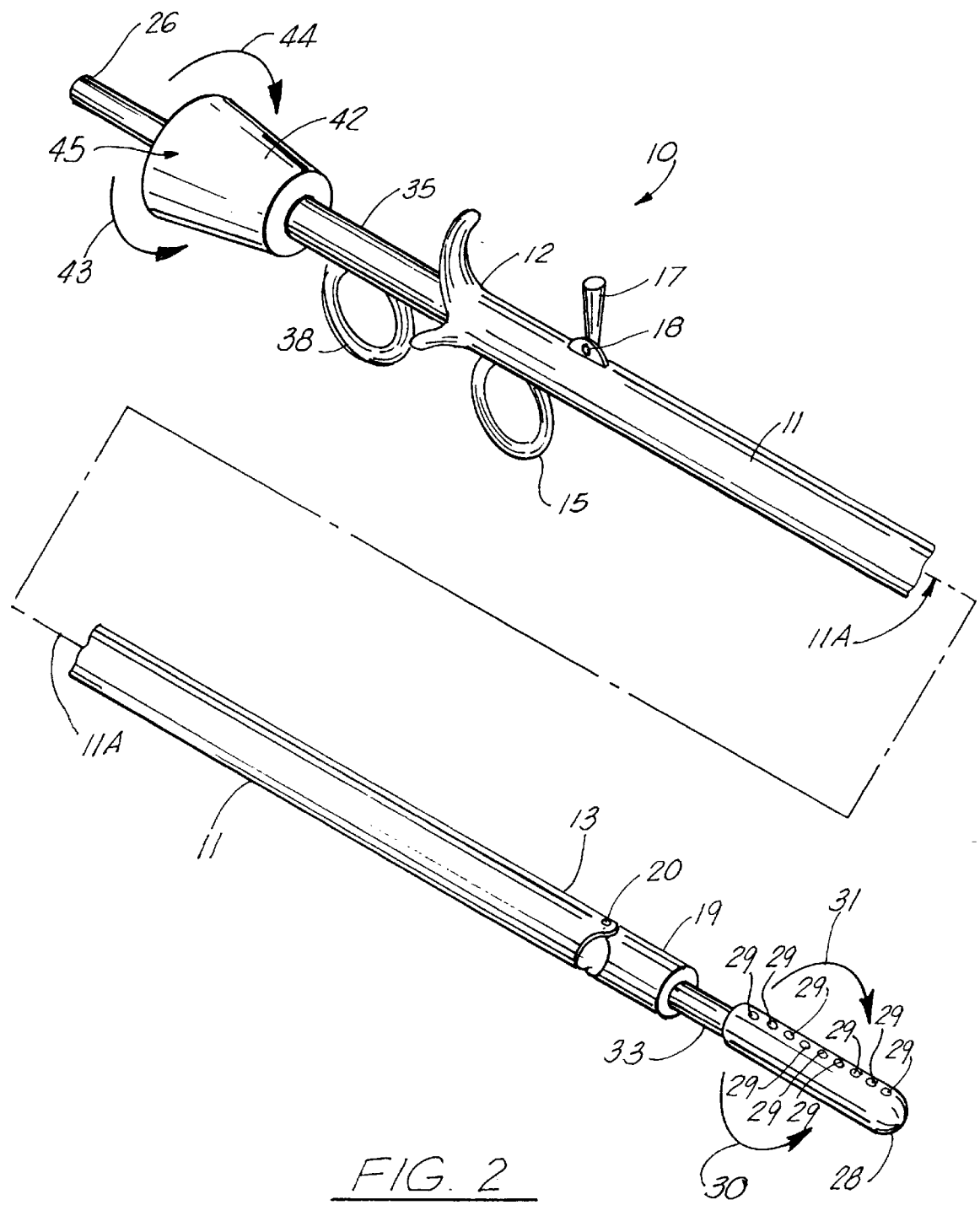
FIG. 2 is a partial perspective view of the preferred embodiment of the apparatus of the present invention.

FIGS. 1 and 2 show generally the preferred embodiment of the apparatus of the present invention designated generally by the numeral 10. Surgical endoscopic instrument 10 includes an elongated instrument body 11 having a proximal end portion 12 and a distal end portion 13. The instrument body 11 provides an open ended, generally cylindrically-shaped bore 14. The proximal end portion 12 can have a handle 15 in the form of a circular ring that can receive one of the surgeon's fingers during use.

An elongated pushrod 16 extends substantially the entire length of bore 14. Pushrod 16 is connected to lever 17 at one portion and to pivoting collar 19 at its other end portion. When the surgeon pivots lever 17, the pushrod 16 moves to pivot or articulate collar 19 relative to its pivotal connection 20 to instrument body 11. The particular construction of a lever 17 for operating a pushrod 16 to articulate a distal end collar portion of an instrument body can be seen in more detail in U.S. Pat. No. 5,503,623, issued to Applicant and entitled "Instrumentation For Laparoscopic Insertion And Application Of Sheet Like Surgical Material," incorporated herein by reference.

Pivotal connection 20 is provided at the connection between instrument body 11 and collar 19. Arrows 21, 22 illustrate the pivotal movement of collar 19 relative to pivot 20 when the surgeon moves lever 17 forward or backward in a pivotal fashion about its pivot connection 18 to body 11.

Collar 19 provides a cylindrically-shaped open ended bore 23 that is preferably sized and shaped to be the same size and shape as the cylindrically-shaped bore 14 of instrument body 11 and to conform generally to the outer surface of tube 25. Arrow 24 in FIG. 1 illustrates a sliding connection that is formed between instrument body 11 and its collar 19 with a selected dispensing tube 25. With the apparatus of the present invention, any one of a number of different dispensing tubes 25 can be inserted into instrument body 11 and collar 19 by placing the proximal end portion 26 of dispensing tube 25 through bore 23 of collar 19 and then into bore 14 of instrument body 11.

A plurality of dispensing tubes 25 are preferably provided, each having a different head 28, each having different patterns of nozzle openings 29. In the embodiment of FIG. 1, the head 28 is an elongated generally cylindrically-shaped head having a plurality of nozzle openings 29 that extend along a line that is preferably parallel to the central longitudinal axis of dispensing tube 25.

At the distal end portion 27 of dispensing tube 25, head 28 begins at annular shoulder 33 and can end distally at a tapered or hemispherically-shaped tip as shown in FIG. 1. With the present invention, dispensing tube 25 and head 28 can be rotated in either rotational direction relative to instrument body 11 as illustrated by arrows 30, 31 in FIG. 2. Also, the surgeon can slide the selected dispensing tube 25 forward or backward relative to instrument body 11. This enables the surgeon to position the nozzle openings 29 in a selected rotational position and in a selected longitudinal position for dispensing a gel, liquid, or medicinal preparation at a location within the patient's body cavity. Further, the articulating connection formed between collar 19 and instrument body 11 allows the surgeon to pivot dispensing head 28 with respect to the central longitudinal axis 11A of the instrument body 11.

The pivoting of collar 19 effects a pivoting of head 28. The dispensing tube 25 is preferably of a flexible material such as rubber or rubber-like plastic at least at the distal 27 end portion thereof. Thus, when the collar 19 articulates about pivot 20 as shown by arrows 21, 22, the dispensing head 28 likewise pivots in the direction of the arrows 21, 22 about pivot 20.

Dispensing tube 25 provides a keyway 32 at its proximal 26 end portion. The keyway 32 registers in a key slot 50 of rotator 42 upon assembly of dispensing tube 25 into bore 14 of instrument body 11. The dispensing tube 25 provides an elongated open ended bore 34 that enables a selected liquid or gel to be conveyed from the proximal 26 end of dispensing tube 25 to the distal 27 end thereof, and to the dispensing openings 29 for dispensing the gel or liquid to a selected position within the body cavity of the patient. Annular shoulder 33 defines a stop that abuts the extreme distal end of the instrument body at collar 19 when the surgeon retracts tube 25 relative to body 11.

Figure 3:
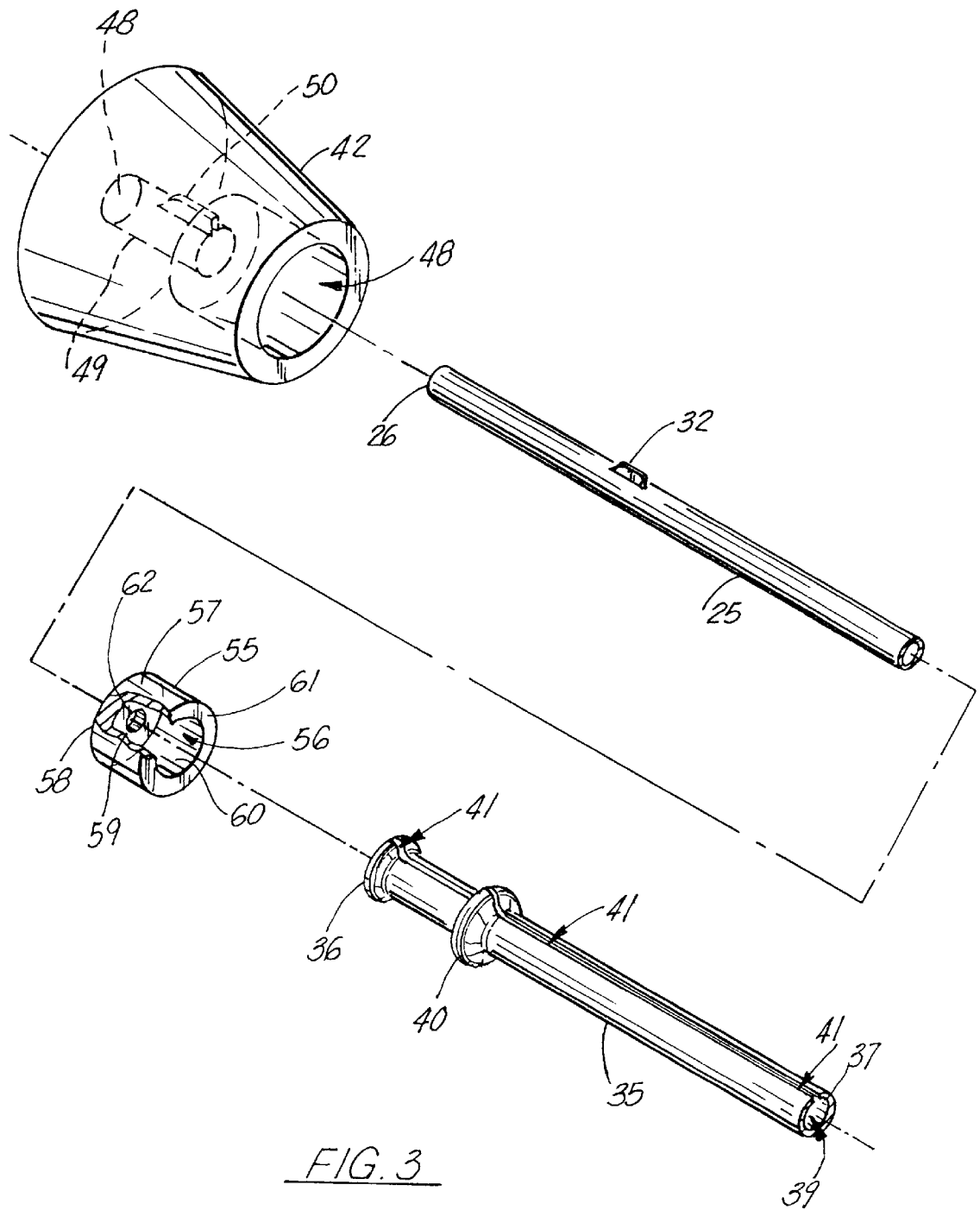
FIG. 3 is a partial perspective exploded view of the preferred embodiment of the apparatus of the present invention.
Figure 4:
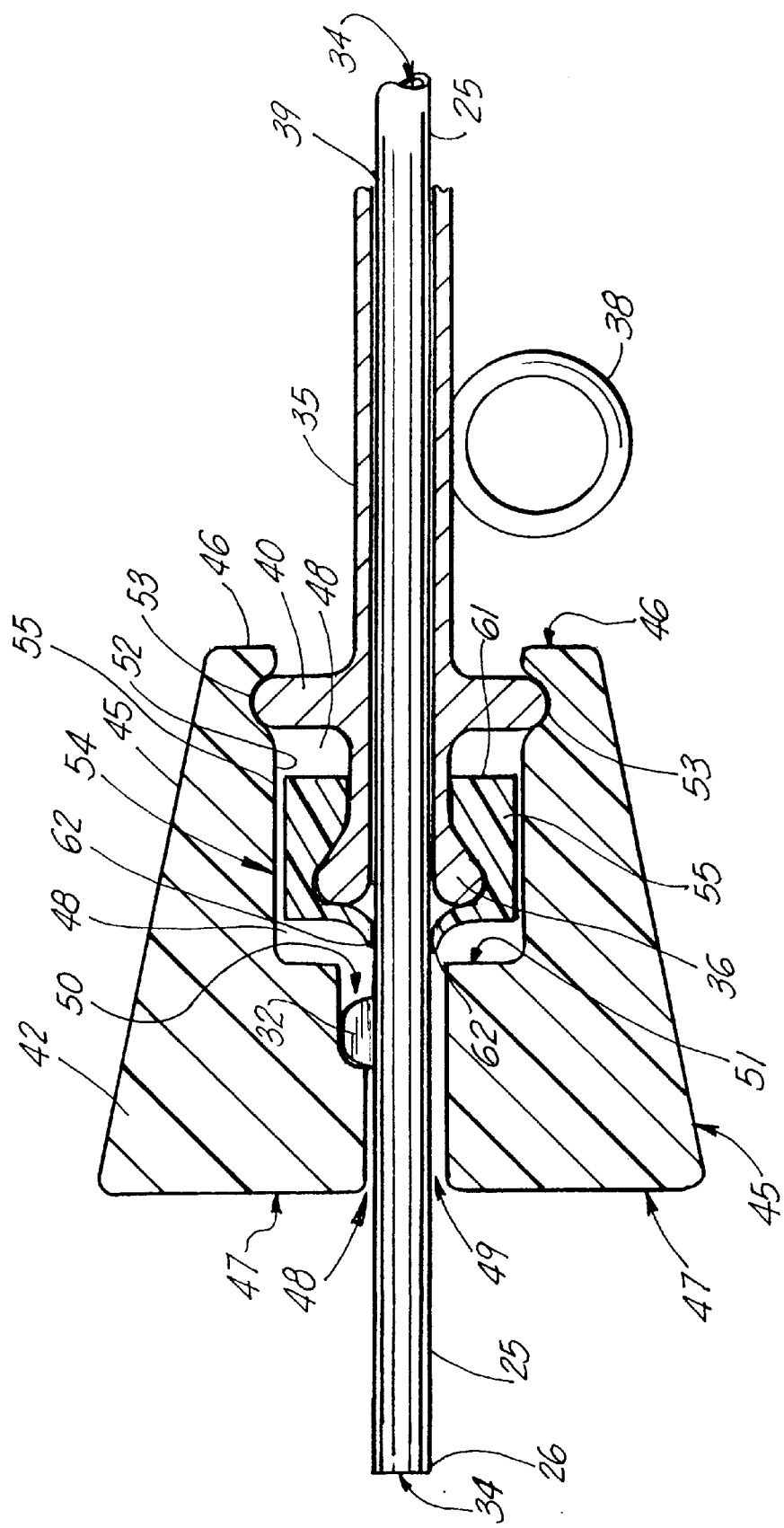
FIG. 4 is a partial sectional view of the preferred embodiment of the apparatus of the present invention.

FIGS. 2–4 illustrate the construction of sealing tube 35 that is placed inside the bore 14 of instrument body 11. Tube 35 also has a bore 39 that receives dispensing tube 25. Sealing tube 35 has a proximal end 36 and a distal end 37. A handle 38 can be provided on the exterior of sealing tube 35, preferably in the form of a circular ring that can be gripped by the surgeon's fingers during use. The dispensing tube 25 is gripped by the sealing tube 35 and its seal member 55 (see FIG. 4).

Since dispensing tube 25 is gripped by and moves with sealing tube 35, the surgeon can grip the handle rings 15, 38 and slide the sealing tube member 35 relative to the instrument body 11 for moving the dispensing head 28 of tube 25 forward and backward as shown by arrow 24 to provide a measure of longitudinal adjustment for positioning of the dispensing head 28 and its nozzle openings 29.

Rotator 42 provides a rotational adjustment for rotating and positioning the dispensing openings 29. As described earlier, lever 17 provides an articulating or pivoting movement of head 28. Thus, three separate adjustments for the positioning of head 28 and its nozzle openings 29 are provided with the apparatus of the present invention. These include rotational adjustment, sliding longitudinal adjustment and pivoting articulating adjustment.

Sealing tube 35 provides an open ended bore 39. Annular rib 40 is positioned on the proximal end portion of the exterior of sealing tube 35. An elongated longitudinally extending slot 41 extends the full length of sealing tube 35. The slot 41 accommodates travel of the keyway 32 of dispensing tube 25 when the dispensing tube 25 is placed through instrument body 11 and into the bore 39 of sealing tube 35 to its final operating position shown in FIG. 4.

FIG. 4 shows the operational positions of dispensing tube 25, sealing tube 35, seal member 55, and rotator 42. Arrows 43, 44 in FIG. 2 illustrate the two rotational directions of rotator 42 that accomplish a corresponding rotation in either direction of head 28 as illustrated by arrows 30, 31 in FIG. 2.

In FIG. 4, rotator 42 provides a frustoconical outer surface 45, a distal flat annular surface 46, and a proximal flat annular surface 47. Bore 48 of rotator 42 accepts dispensing tube 25, the distal end portion of sealing tube 35, and seal member 55, as shown in FIG. 4. Bore 48 has a smaller diameter section 49 that is generally cylindrically shaped that communicates with key slot 50.

A larger diameter section of bore 48 is provided at annular surface 51 and cylindrically-shaped inner surface 52. An annular groove 53 receives the outermost surface of annular rib 40. This provides a relatively loose fit so that the rib 40 rotates with respect to rotator 42 at annular groove 53.

A gap 54 is provided in between cylindrical inner surface 52 and seal member 55 so that rotator 42 does not engage and rotate with seal member 55. Thus, the rotator 42 only engages and rotates with dispensing tube 25 because of the connection between keyway 32 and key slot 50.

In FIG. 3, the construction of seal member 55 is shown in more detail. Seal member 55 includes an open socket portion 56, an outer cylindrical surface 57, and an annular disk 58 having an opening 59 therethrough. The opening 59 allows dispensing tube 25 to pass therethrough as shown in FIG. 4. However, opening 59 is preferably slightly smaller in diameter than the diameter of dispensing tube 25 so that the annular disk 58 slightly deforms as shown in FIG. 4 to form a seal at sealing surface 62 with dispensing tube 25. The seal member 55 is preferably of a rubber, silicone, or rubber-like plastic construction. Seal member 55 has an inner surface 60 that is generally cylindrically shaped and an outer edge 61 that surrounds socket 56.

During use, the surgeon can select a particular dispensing tube 25 with a head 28 having a desired pattern of openings 29. The openings 29 can be of a desired number and of variable diameters and can be positioned over head 28 in a desired array or pattern. The construction of different types of spray heads and spray patterns through openings or nozzles is disclosed more fully in prior copending patent application Ser. No. 08/718,861, filed Sep. 24, 1996, incorporated herein by reference.

During use, the surgeon selects a particular dispensing tube 25 and inserts the proximal 26 end into the bore 23 of collar 19 and into the bore 14 of instrument body 11. The proximal end 26 of dispensing tube 25 then is placed into the bore 39 of sealing tube 35 as shown in FIG. 4. Sealing tube has an outer diameter that is smaller than or equal to the diameter of bore 14 of instrument body 11. Thus, the inner tube of the assembly of instrument 10 is tube 25. Sealing tube 35 fits over dispensing tube 25 as shown in FIG. 4. The assembly of dispensing tube 25 and sealing tube 35 is accomplished by placing sealing tube into the bore 14 of body 11 at its distal end 13 while placing the distal end 37 of sealing tube 35 into the bore 14 of body 11 at proximal end 12. Thus, instrument body 11 is the outermost tube.

The keyway 32 of tube 25 registers in the key slot 50 of rotator 42. Seal member 55 is placed over the ring 63 at the proximal end of sealing tube 35 before dispensing tube 25 is inserted into the bore 39 of sealing tube 35.

Once the apparatus is assembled as shown in FIGS. 1–4, the surgeon can place the entire assembly through a surgically formed opening in a patient's body cavity such as in the abdominal wall or chest wall of a patient. For example, the surgeon can, if desired, place the instrument 10 through a commercially available porting device having a valve at its proximal end portion as disclosed more particularly in U.S. Pat. No. 5,503,623 and designated therein as part numbers 14 and 18.

Figure 5:
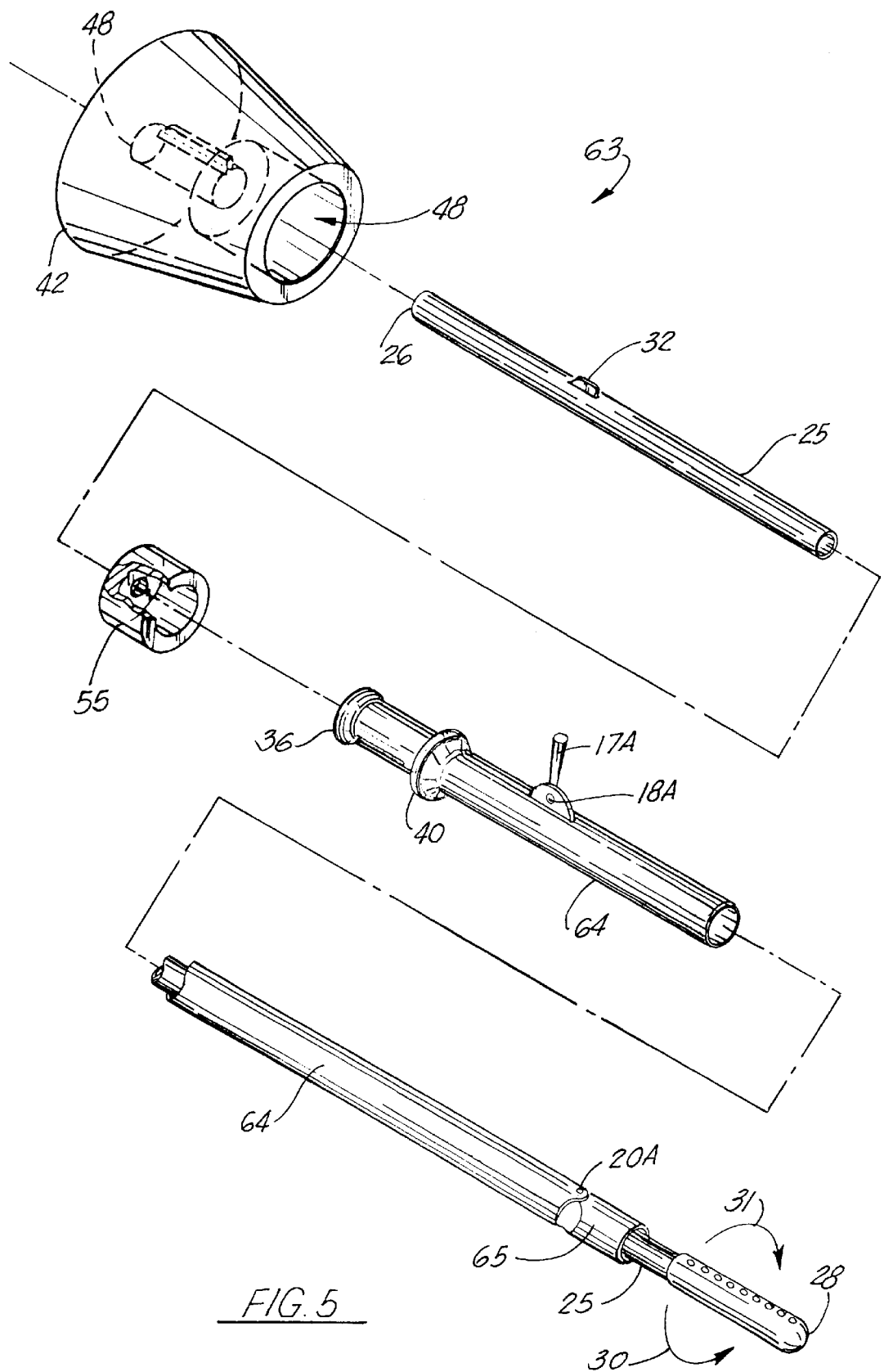
FIGS. 5-6 are perspective, exploded views of a second embodiment of the apparatus of the present invention.
Figure 6:
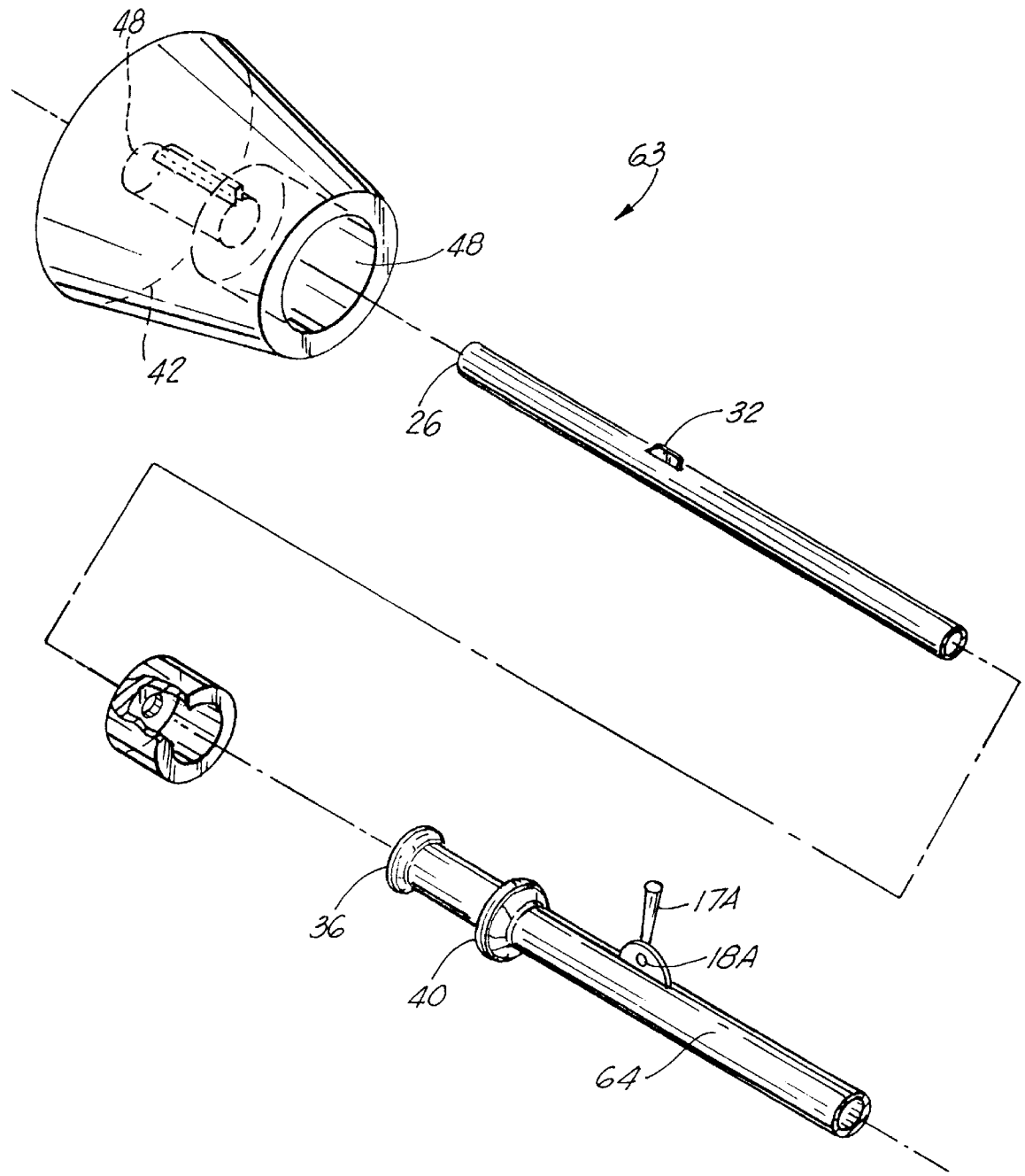

In FIGS. 5 and 6, an alternate embodiment of the apparatus of the present invention is shown, designated generally by the numeral 63 in FIGS. 5 and 6. In the embodiment of FIGS. 5 and 6, an instrument body 64 is constructed so that is a combination of the instrument body 11 and sealing tube 35 of the preferred embodient. Thus, the instrument body 64 in FIGS. 5 and 6 has a proximal end 36 in the form of an annular ring that forms a seal with the seal member 55 in the same fashion that the sealing tube 35 forms such a seal, as shown in FIG. 4. Similarly, the annular ring 40 of instrument 64 forms a connection with the annular groove 53 of rotator 42 as with the embodiment of FIGS. 1–4, shown more particularly in FIG. 4. However, in the embodiment of FIGS. 5 and 6, a lever 17A and its pivotal connection 18A are provided so that the instrument body 64 includes a pushrod for articulating a collar 65 in the same fashion that the pushrod 16 in the embodiment of FIGS. 1–4 is operated by the lever 17 to articulate collar 19 relative to instrument body 11. In the embodiment of FIGS. 5 and 6, the sealing tube 35 of FIGS. 1–4 has basically been eliminated. Rather, the sealing portions of the device are provided on the proximal end of the instrument body 64.

Figure 7:
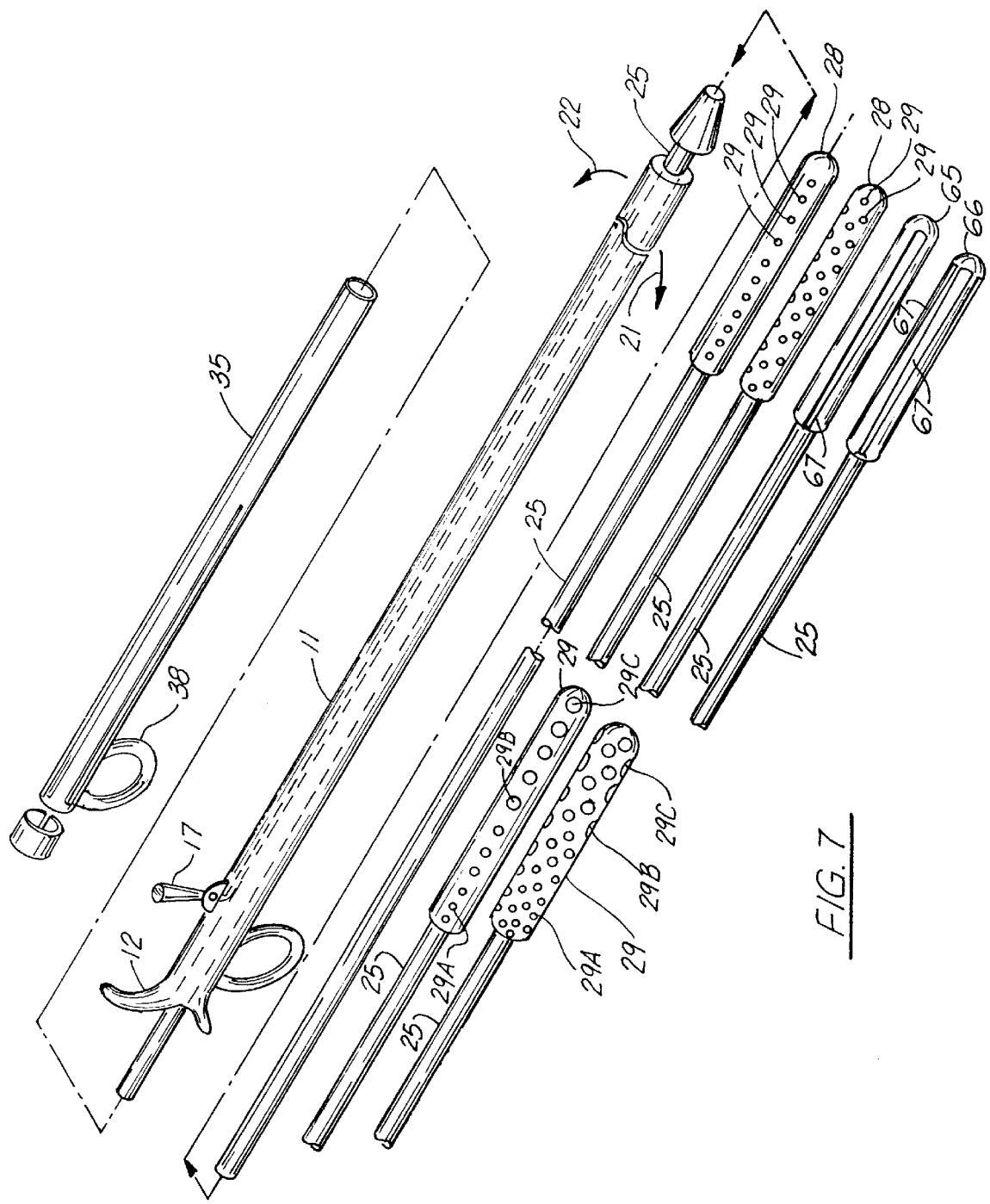
FIG. 7 is a perspective view of the preferred embodiment of the apparatus of the present invention showing various dispensing heads and different nozzle opening patterns and slot shaped dispensing patterns.

In FIG. 7, various dispensing heads 28, 65, 66 are shown as are a variety of hole patterns and slotted dispensing opening patterns that can be used at the distal end of a dispensing tube 25. The dispensing head 28 can have a single row of openings 29 or an array of openings 29 that cover the head 28. The head 28 can be covered with holes 29A, 29B, 29C of various opening diameters such as small openings 29A, medium sized openings 29B, and large openings 29C. The openings 29A, 29B, 29C can be in a single row or spaced over the entire head 28. The holes 29 can gradually increase in size along a proximal to distal line, or along a distal to proximal line.

Slots 67 can be provided for dispensing. In FIG. 7, head 65 has a single longitudinally extending dispensing slot 67. Head 66 has a plurlaity of circumferentially spaced dispensing slots 66.

The following table lists the parts numbers and parts descriptions as used herein and in the drawings attached hereto.

PARTS LIST

| Part Number | Description |
| --- | --- |
| 10 | surgical instrument |
| 11 | instrument body |
| 11A | central longitudinal axis |
| 12 | proximal end portion |
| 13 | distal end portion |
| 14 | open ended bore |
| 15 | handle |
| 16 | pushrod |
| 17 | lever |
| 17A | lever |
| 18 | pivot |
| 18A | pivot |
| 19 | collar |
| 20 | pivotal connection |
| 20A | pivotal connection |
| 21 | arrow |
| 22 | arrow |
| 23 | open ended bore |
| 24 | arrow |
| 25 | dispensing tube |
| 26 | proximal end |
| 27 | distal end portion |
| 28 | head |
| 29 | nozzle openings |
| 29A | smaller opening |
| 29B | medium opening |
| 29C | large opening |
| 30 | arrow |
| 31 | arrow |
| 32 | keyway |
| 33 | annular shoulder |
| 34 | bore |
| 35 | sealing tube |
| 36 | proximal end |
| 37 | distal end |
| 38 | handle |
| 39 | open ended bore |
| 40 | annular rib |
| 41 | slot |
| 42 | rotator |
| 43 | arrow |
| 44 | arrow |
| 45 | frustoconical outer surface |
| 46 | flat annular surface |
| 47 | flat annular surface |

PARTS LIST -continued

| Part Number | Description |
| --- | --- |
| 48 | bore |
| 49 | smaller diameter section |
| 50 | key slot |
| 51 | annular surface |
| 52 | cylindrical inner surface |
| 53 | annular groove |
| 54 | gap |
| 55 | seal member |
| 56 | socket |
| 57 | outer cylindrical surface |
| 58 | annular disk |
| 59 | opening |
| 60 | inner surface |
| 61 | annular edge |
| 62 | sealing surface |
| 63 | surgical instrument |
| 64 | instrument body |
| 65 | head |
| 66 | head |
| 67 | slot |

The foregoing embodiments are presented by way of example only; the scope of the present invention is to be limited only by the following claims.

I claim:

1. A method of dispensing a selected liquid, gel or like medicinal material into the patient's body cavity, comprising the steps of:

a) surgically forming a port through the patient's body cavity wall;

b) said placement of said port including placing a first tubular member, having proximal and distal end portions and an elongated bore into the patient's body cavity;

c) inserting a second tubular member into the bore of the first tubular member, the second tubular member being an instrument body with a distal end portion with a nozzle that can be rotated by the surgeon with respect to the first tubular member, is the second tubular member having a central axis, an outer wall, and a row of dispensing openings positioned along a line generally parallel to the central axis;

d) extending the distal end of the second tubular member and its nozzle into the patient's body cavity;

e) rotating the nozzle to enable a surgeon to position the distal end in a desired rotational position for aiming a spray; and f) transmitting the liquid into the patient-s body cavity via the nozzle.

2. The method of claim 1 wherein in step "f", the surgeon can selectively articulate the instrument body distal end to flex the distal end of the dispensing tube and the nozzle.

3. The method of claim 1 wherein the second tubular body is generally cylindrically shaped, and includes said moving distal end portion, the entire length of said second tubular body having an open ended bore and further comprising the step of pivoting the distal end portion in order to flex the dispensing tube.

4. The method of claim 1 wherein the second tubular member is a dispensing tube that is flexible at least at the distal end portion thereof.

5. The method of claim 1 wherein in step "b" there are a plurality of dispensing tubes as part of a "kit", a selected one of the dispensing tubes defining the second tubular member, each tube having a nozzle end portion with a nozzle spray pattern, that differs from the spray pattern of the other dispensing tubes, and in steps "c" and "d" the surgeon selects a dispensing tube from the plurality of dispensing tubes with the desired nozzle spray pattern.

6. The method of claim 1 further comprising the step of enabling the surgeon to rotate the nozzle by manipulating the proximal end portion of the instrument body.

7. The method of claim 1 wherein the dispensing openings are of different diameters.

8. The method of claim 1 wherein the dispensing openings are linearly aligned.

9. The method of claim 5 wherein each dispensing tube is longer than the instrument body and further comprising the step of sliding the dispensing tube relative to the instrument body during a positioning of the nozzle relative to a desired location within the patient's body cavity.

10. The method of claim 1 wherein the instrument body has a rotator at its proximal end for rotating the second tubular member and further comprising the step of rotating the nozzle to a desired rotational position using the rotator.

11. The method of claim 9 wherein the rotator is operable by the surgeon externally of the patient's body cavity when the nozzle is positioned inside the patient's body cavity.

12. An endoscopic surgical instrument comprising:
   a) a surgical delivery tube that can be surgically placed through a surgical opening in a patient's body cavity wall, said tube having a bore;
   b) an instrument body that can be placed in the bore of the tube, and having proximal and distal end portions and an instrument body bore;
   c) a dispensing tube that has proximal and distal end portions, the dispensing tube being sized and shaped to fit the instrument body bore;
   d) a nozzle at the distal end of the dispensing tube for dispensing liquids, gels, and like medicinal materials into a patient's body cavity in a selected radial direction;
   e) the distal end of the instrument body including a rotator that is rotatable into multiple positions, the rotator being coupled to the dispensing tube so that the distal end portion of the dispensing tube also rotates with the rotator; and
   f) a bore for transmitting fluid between the proximal and distal end portions of the dispensing tube when the tube occupies the bore of the instrument body and the nozzle is positioned within the patient's body cavity.

13. The instrument of claim 12 further comprising a syringe and a flexible extension tube that is positioned in between the syringe and the proximal end of the dispensing tube, for enabling a surgical assistant to dispense a gel, liquid, medicine or the like from the syringe into the extension tube and dispensing tube while the surgeon aims and positions the distal end of the dispensing tube.

14. The instrument of claim 12 wherein the instrument body has an open ended bore that extends from the proximal end, through the rotator to the distal end.

15. The instrument of claim 12 wherein the dispensing tube is slidably mounted within the instrument body bore.

16. The instrument of claim 12 wherein the instrument body comprises a pair of body sections including a smaller diameter section and a larger diameter section.

17. The instrument of claim 16 wherein each of the sections has a bore.

18. The instrument of claim 12 wherein each of the nozzles has a plurality of openings having different respective spray patterns.

19. The instrument of claim 19 wherein the nozzle has an array of openings spaced along one side portion of the nozzle.

20. The instrument of claim 12 wherein there are a plurality of flexible dispensing tubes defining a kit, each being sized and shaped to fit the instrument body bore, each having a nozzle with a selected spray pattern so that a surgeon can select a desired spray pattern by selecting a particular dispensing tube and inserting said selected tube into the instrument body bore.

21. The instrument of claim 12 wherein the instrument body is generally cylindrically shaped.

22. The instrument of claim 12 wherein the dispensing tube is of a flexible rubber-like material at least at the distal end portion thereof.

23. The apparatus of claim 12 wherein the openings are of different diameters.

24. The apparatus of claim 12 wherein on at least one of the dispensing tubes the openings are linearly aligned and parallel to the bore of the dispensing tube.

25. The apparatus of claim 12 wherein the dispensing tube distal end portion is flexible.

26. A surgical instrument that can be placed through a surgical opening in a patient's body cavity wall, comprising:
   a) an instrument body that can be placed through the surgical opening, the body having proximal and distal end portions and an instrument body bore;
   b) a kit that includes a plurality dispensing tubes that each have proximal and distal end portions, each dispensing tube being sized and shaped to fit the instrument body bore and at least some of the dispensing tubes being flexible at least at the distal end portion thereof;
   c) a nozzle at the distal end of each of the dispensing tubes for dispensing liquids, gels, and like medicinal materials into a patient's body cavity;
   d) the distal end of the instrument body including a rotator that is rotatable into multiple positions, the rotator being removably connectable to a selected of the dispensing tubes so that the distal end portion of the dispensing tube also rotates with the rotator during use; and
   e) a bore for transmitting fluid between the proximal and distal end portions of each dispensing tube when a selected of the tubes occupies the bore of the instrument body and the nozzle is positioned within the patient's body cavity.

* * * * *